US006692627B1

United States Patent
Russell et al.

(10) Patent No.: US 6,692,627 B1
(45) Date of Patent: Feb. 17, 2004

(54) ELECTRICAL FIELD FLOW FRACTIONATION (EFFF) USING AN ELECTRICALLY INSULATED FLOW CHANNEL

(75) Inventors: Dale R. Russell, Boise, ID (US); Michael W. Hill, Boise, ID (US)

(73) Assignee: Boise State University, Boise, ID (US)

( * ) Notice: Subject to any disclaimer, the term of this patent is extended or adjusted under 35 U.S.C. 154(b) by 0 days.

(21) Appl. No.: 09/676,301

(22) Filed: Sep. 26, 2000

(51) Int. Cl.⁷ .............................................. B01D 17/06
(52) U.S. Cl. ...................... 204/554; 204/573; 204/660; 204/665
(58) Field of Search ................................ 204/554, 573, 204/660, 665

(56) References Cited

U.S. PATENT DOCUMENTS 3,849,275 A * 11/1974 Candor ........................ 204/554
4,722,787 A * 2/1988 Fombarlet et al. ........... 204/665
5,036,365 A * 7/1991 Landa ......................... 204/665
6,136,171 A * 10/2000 Frazier et al. ............... 204/450

* cited by examiner

Primary Examiner—Arun S. Phasge
(74) Attorney, Agent, or Firm—Pedersen & Co., PLLC; Ken J. Pedersen; Barbara S. Pedersen

(57) ABSTRACT

The present invention is an apparatus and a process for separation and resolution of particles suspended in, or molecules dissolved in, a sample mixture or solution using electrical field flow fractionation (EFFF). Fractionation of individual components in the mixture/solution is obtained by the interaction of particles/molecules with an electric field applied perpendicular to the flow direction, and externally to the fractionation channel. The plate electrodes are electrically isolated from the sample and carrier within a thin, non-permeable, insulating coating on the inside surfaces electrodes. This coating forms a barrier between the solution phase and the electric circuit used to generate the working electric field. The flow channel is formed by sandwiching a shaped insulating gasket between the two parallel plate electrodes. The side walls of the channel are defined then by the inside walls of the shaped, insulating gasket.

3 Claims, 5 Drawing Sheets

ELECTRICAL FIELD FLOW FRACTIONATION (EFFF) USING AN ELECTRICALLY INSULATED FLOW CHANNEL

BACKGROUND OF THE INVENTION

1. Field of the Invention

This invention relates generally to field flow fractionation technology. More particularly this invention relates to a method of and apparatus for electric field flow fractionation wherein the fractionation flow channel is electrically insulated from the applied electrical field.

2. Related Art

Field flow fractionation (FFF) was first described in the patent literature in U.S. Pat. No. 3,449,938 (Giddings). Fractionation of components in a mixture was achieved by applying a temperature gradient between the top and bottom plates of a fractionation flow channel. Since then, separation has been achieved by the use of various types of force fields. A general method for separation by FFF is: A ribbon shaped flow channel is created by sandwiching a shaped gasket between two parallel plates (channel walls). The channel is typically long in the axial dimension, i.e., for analytical purposes, about 10–100 cm long in the direction of fluid flow. A typical channel has a width of 1–2 cm and a height of 25–200 $\mu$m. The fractionation field is imposed perpendicular to the length and width, and parallel to the channel height. Due to capillary effects, a parabolic flow profile develops between the top and bottom plates. A sample is injected into the carrier stream prior to entering the channel, and the sample components are monitored downstream of the channel exit port.

With conditions of laminar flow, the fluid flow velocity within the channel is a function of distance from the channel walls. The fluid flow velocity is at a maximum at a position midway between the top and bottom plates, and is at a minimum at the channel walls. When a fractionation field is applied perpendicular to the direction of laminar flow, any particle/molecule that interacts with the force will be forced to one or the other wall of the channel. However, particle/molecule accumulation at a wall cannot continue indefinitely, as particulate/molecular mass diffusion acts to counter the buildup of concentration at the wall. The two competing processes come to equilibrium, creating a Gaussian concentration distribution at a characteristic distance from the wall. This characteristic distance depends on the type of particle/molecule and its interaction strength with the field, and the particles/molecules diffusion rate in the carrier. A particulate/molecular distribution centered close to the wall will be in a slower moving laminae than one centered midway between the walls. The distribution centered midway between the walls will be moving faster through the channel and thus, it will exit the channel prior to the distribution centered near the wall.

Early demonstrations of an electric field applied to an FFF flow channel used a semipermeable membrane for the channel walls, with the electrodes positioned externally A later EFFF channel design used graphite plate electrodes, (U.S. Pat. No. 5,240,618 Caldwell et al.) The carrier solution used in this latter case was either deionized water or an aqueous solution containing a red-ox couple such as quinone/hydroquinone. In both of these examples there was an electrical current flow across the channel.

SUMMARY OF THE INVENTION

The present invention is an apparatus and a process for separation and resolution of particles suspended in, or molecules dissolved in, a sample mixture using electrical field flow fractionation (EFFF). Fractionation of individual components in a mixture/solution is obtained by the interaction of particles/molecules with an electric field applied perpendicular to the flow direction, and externally to the fractionation flow channel. A parabolic flow profile is established between two conducting plate electrodes. The plate electrodes are electrically isolated from the sample and carrier with a thin, non-permeable, insulating coating on the inside surfaces of the electrodes (channel walls). This coating forms a barrier between the solution phase and the electric circuit used to generate the applied electric field.

The flow channel is formed by sandwiching a shaped insulating gasket between the two zparallel plate electrodes. The side walls of the channel are defined then by the inside walls of the shaped gasket. The top and bottom walls are formed by the two, coated, parallel plate electrodes. The channel has an inlet port at one end, and an outlet port at the opposite end. A carrier fluid comprising either water or an organic solvent is pumped in the channel through the inlet port, and it exits out the outlet port. A sample is mixed with the carrier liquid prior to entering the channel and the sample is monitored for separation of the particles/molecules downstream of the exit port.

DESCRIPTION OF THE PREFERRED EMBODIMENTS

All the known prior demonstrations of particulate/molecular separation using EFFF were done using a channel design that employed conducting electrodes or ion permeable membranes for the channel walls. Both of these designs allow charge transfer across the channel boundary. Insulator coated aluminum walls, on the other hand, allow an electric field to be applied across the channel, but do not allow charge transfer across the channel boundary. In addition, the insulator coating reduces chemical and physical interactions between the analyte particles and the channel walls. The insulator may be polytetrafluoroethylene (PTFE) or any other nonconductor.

Charge transfer across the channel boundary causes a current to flow through the charging circuit. Current measurements can be used as an indication that there is movement of the charge carriers within the channel, which may be useful information. But, the presence of current also indicates that electrochemical processes are occurring at the channel surface, and this is a detrimental effect of the conducting channel walls. Current also means some species are undergoing reduction-oxidation (redox) processes. In this case, the analyte could be undergoing reductive or oxidative processes that alter its identity. Electrical FFF separates charged particles through their interaction with the applied electric field. If the charged particles migrate toward the channel wall and lose their charge, they may continue to move down the channel, but with no charge, and diffusion alone acts to re-disperse them. This will cause unwanted band broadening and loss of resolving power of the instrument.

Particles with like charge will tend to repel each other which acts to reduce particle flocculation. If the particles lose their charge, particle flocculation is more likely, i.e., interparticle adhesion and adhesion to the channel wall are more likely to occur. The configuration disclosed herein circumvents all of these adverse conditions and permits effective particle separation and analysis based upon size and electrophoretic mobility.

Figure 1:
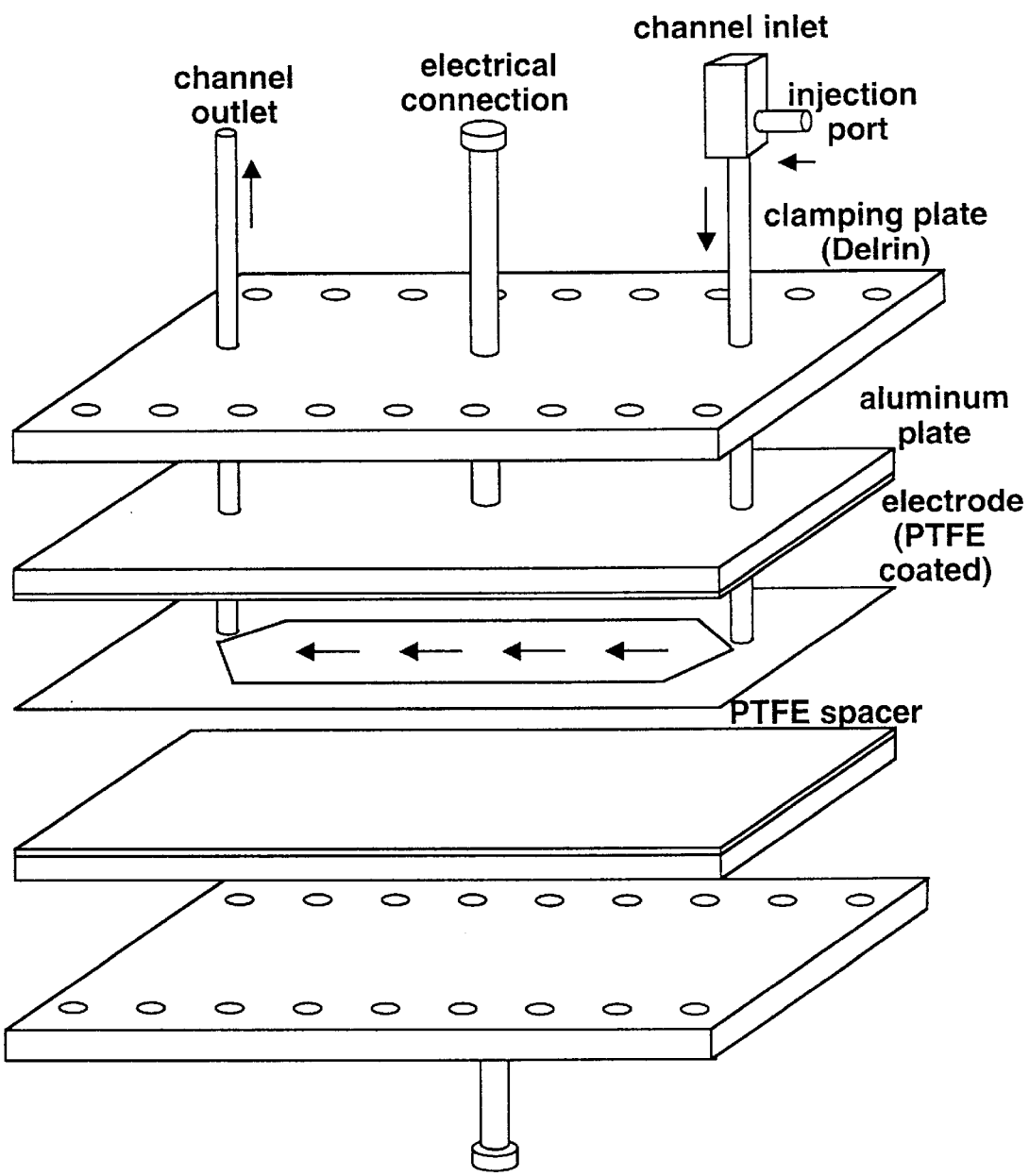
FIG. 1 is a schematic, perspective view of an EFFF device using an electrically insulated fractionation flow channel according to the present invention.

A schematic of the EFFF apparatus and process of the present invention is shown in FIG. 1. The design employs a ribbon shaped channel that is obtained by sandwiching a shaped electrically insulating gasket between two parallel plate electrodes. The electrodes are insulated from the carrier liquid with a thin layer of PTFE, which serves to eliminate any charge transfer processes from occurring across the electrode boundary. Inlet and outlet ports at the apex at each end of the channel permit fluid flow through the channel. The channel dimensions are typically 125 $\mu$m (height)×67 cm (length)×1 cm (width). Due to the high aspect ratio of the channel, a parabolic flow profile develops across the narrow height dimension. This is shown in FIG. 2.

Figure 2:
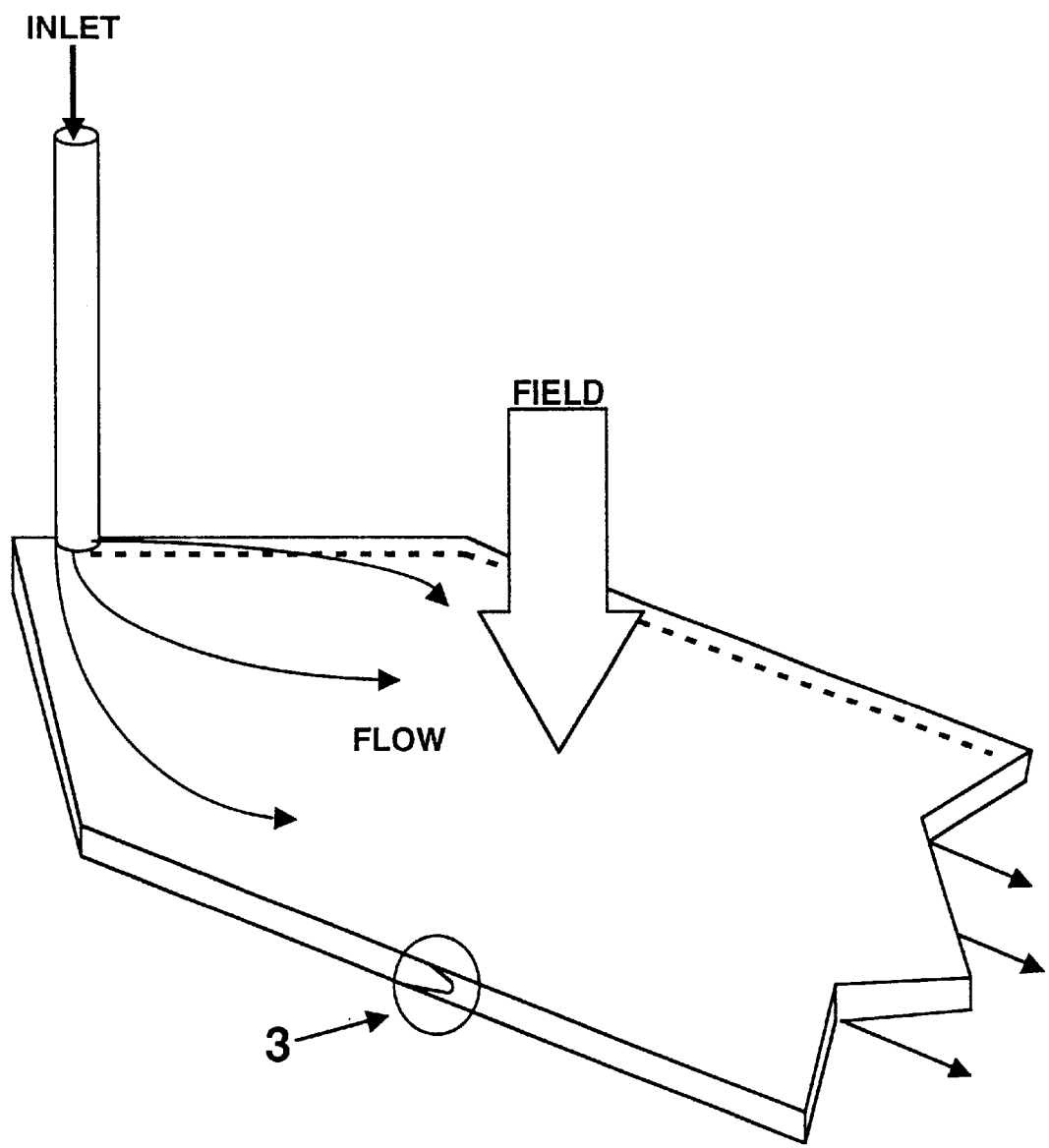
FIG. 2 is a detail, schematic view of the flow of a sample in a device according to FIG. 1.
Figure 3:
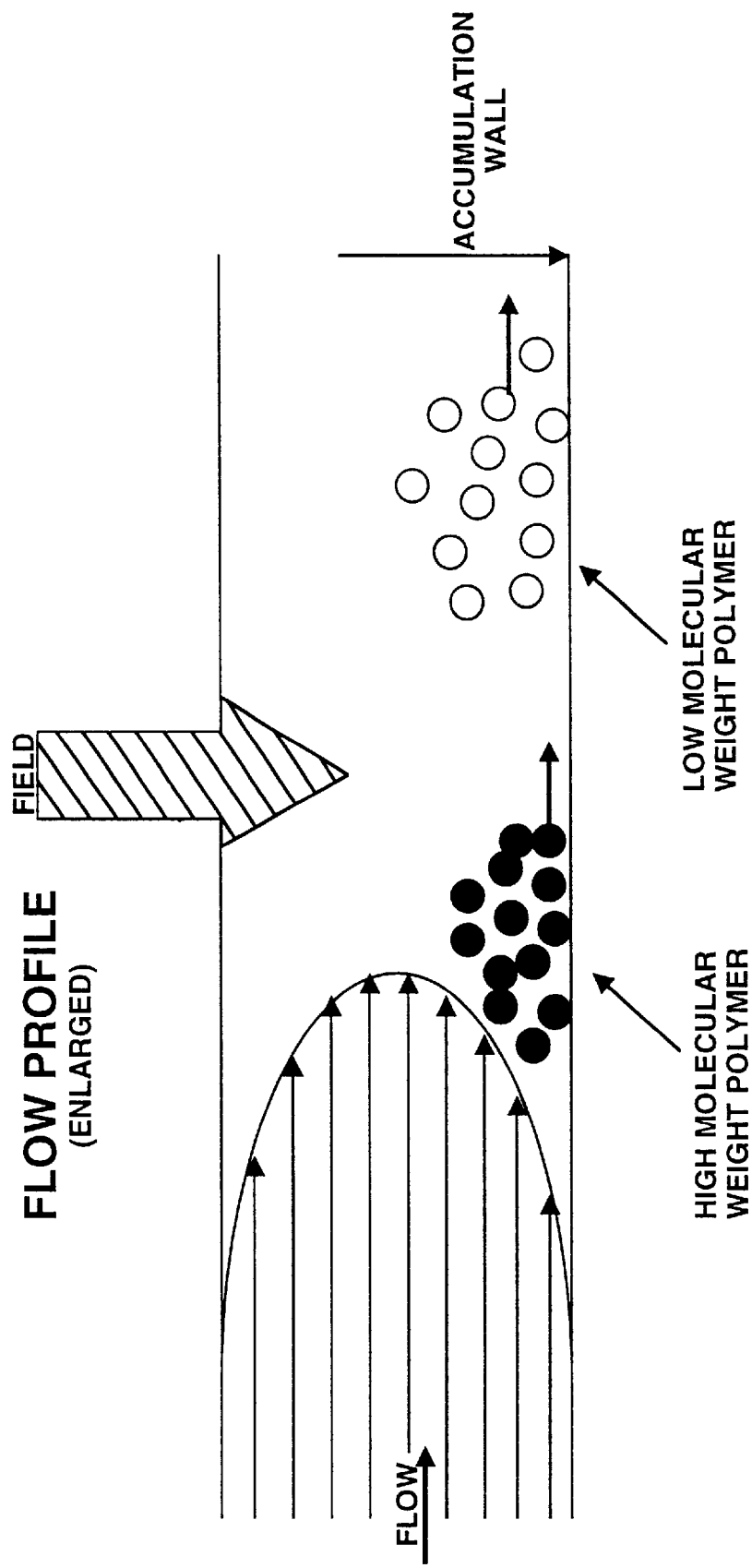
FIG. 3, is an enlarged, side schematic view of the flow profile from FIG. 2.

An enlarged, side schematic view of the flow profile from FIG. 2 is schematically shown in FIG. 3. In FIG. 3 a high molecular weight polymer (more influenced by the fractionation field) is separated from a low molecular wight polymer (less influenced by the fractionation field).

EXAMPLE 1

For analytical purposes, an Alltech model 301 HPLC pump is used to pump the carrier solution through the channel, and an HP series 1050 UV detector is used in combination with a Wyatt Technology miniDAWN to detect and size eluting particles. A Rheodyne model 7725 seven port sample injection valve is used to inject typically a 20 $\mu$L sample into the channel. An HP model 33120A function generator is used to establish, monitor and control the electrostatic potential across the channel.

One carrier (solvent) for use in this work is Norpar-12™, available from Exxon Corporation. This is a normal paraffinic hydrocarbon with average chain length of 12 carbons and a conductivity of <0.1 pmho. The fractionation cell filled with this solvent behaves very much like a capacitor, and I/E calculations may be approximated using standard formulas. The preferred carrier solution used is Norparm with a non ionic surfactant Triton N-42 and a zirconium metal soap.

A solution of soluble zirconium hexadecanoate (Hex-CeM™) is available from Mooney Chemical (Cleveland, Ohio). Dispersions of various pigments, including Sun Fast Blue, Sun Brite Yellow and Sun Brite Maroon, all from Sun Chemical, are typically dispersed into NorparTm as electrophotographic toners.

The focus of this experiment was to separate toner particles by electrophoretic mobility with EFFF.

Figure 4:
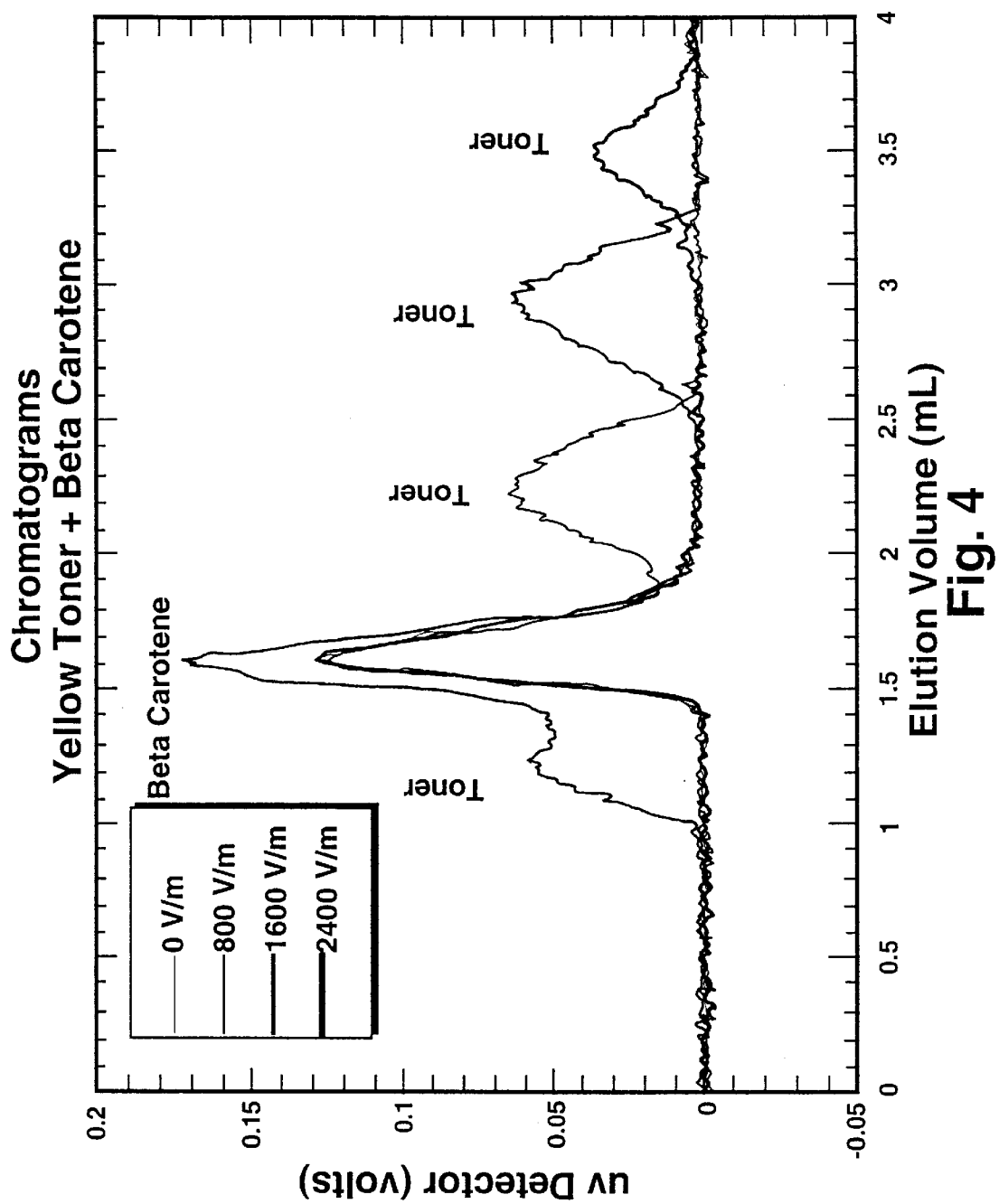
FIG. 4 is a graph of the output from an analyzer of the exit port from a device according to FIG. 1 operating on beta carotene and yellow toner.
Figure 5:
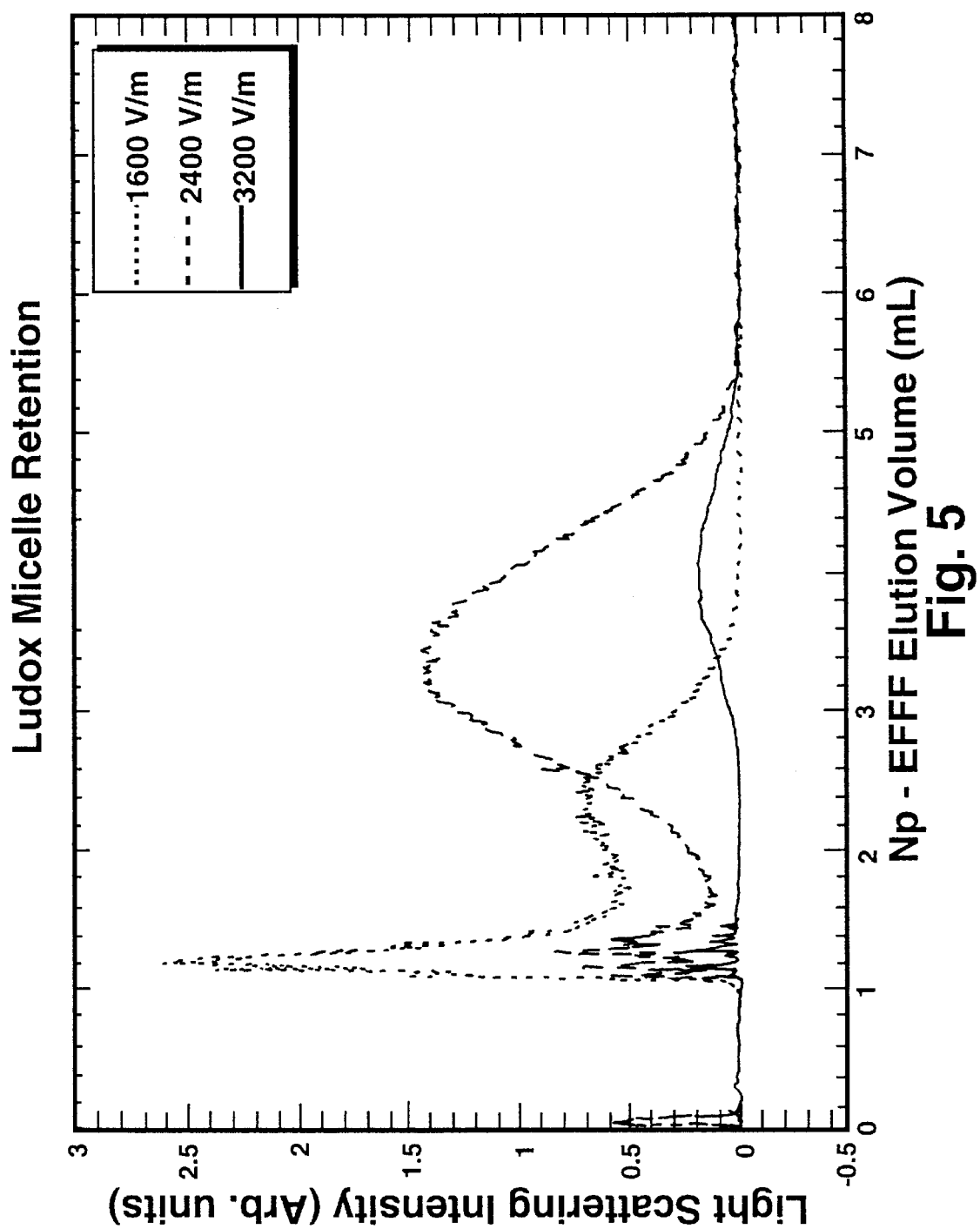
FIG. 5 is a graph of the output from an analyzer of the exit port from a device according to FIG. 1 operating on inverse micelles of Ludox™ in $H_2O$/AOT dodecane.

EFFF enables us to separate components in a mixture by differences in the strength of the coupling of the analyte particles between the electrostatic field and the particles' diffusivity. If the coupling between the field and particle is weak, or if the particle is a fast diffuser, then there may be no measurable retention. The greater the particle field interaction or the slower the diffusion rate, the greater the retention. This is shown in FIG. 4. A mixture of beta carotene and yellow toner particles is separated due to differences in electrophoretic mobility and diffusion rate. Beta carotene is a small uncharged molecule, and it is not retained. Thus, beta carotene can be used to determine the channel void volume, i.e., the geometric volume of the channel, or the volume of carrier required to elute an unretained species. The yellow toner particles are retained, and the retention volume can be seen to depend on the field strength. The beta carotene peak position is invariant with field strength and it is always observed at 1.63 mL. This is the void volume of the channel.

EXAMPLE 2

Another advantage of the Np-EFFF channel is the ability to separate and characterize micellar structures. In this instance, we have demonstrated the retention of reverse micelles according to the ratio of their electrophoretic mobilities and diffusivities. A micelle is defined as a small droplet of one solvent suspended in a second, immiscible solvent. "Micelle" is usually assumed to mean a non-aqueous droplet suspended in an aqueous medium. Reverse (or "inverse") micelles are usually understood to mean water droplets suspended in a non-aqueous solvent. Either or both liquids may contain other solutes as well, and could therefore be a solution. The figure shows retention of inverse micelles. The sample consisted of a 10% aqueous LudoX™ solution suspended in a solution of dodecane and the non-ionic surfactant AOT. Retention volume increases with field strength, according to theory, showing the separation of the micelles according to size, electrophoretic mobility and diffusitivity.

Due to the fragility of micellar structures, there are very few methods of characterizing them without destroying them. Chromatographic and centrifugation methods are too aggressive. The shear forces of these aggressive methods destroy the micelles. In contrast, the Np-EFFF channel separate the micelles, and can be used to determine micelle size distribution and re-organization rates, for example.

Although this invention has been described above with reference to particular means, materials and embodiments, it is to be understood that the invention is not limited to these disclosed particulars, but extends instead to all equivalents within the scope of the following claims.

We claim:

1. An EFFF apparatus, comprising a pair of parallel plate electrodes external to and electrically isolated from a fractionation flow channel in saud EFFF aooaratus by an insulating coating on the inside surfaces of the electrodes, wherein said fractionation flow channel is defined by side walls of an insulating gasket sandwiched between the two plate electrodes and by top and bottom walls formed by the coated inside surfaces of the two electrodes.

2. The apparatus of claim 1 wherein the coating is a PTFE coating.

3. An EFFF process wherein a pair of parallel plate electrodes are external to and electrically isolated from a fractionation flow channel that is defined by side walls of an insulating gasket sandwiched between the two plate electrodes, and by top and bottom walls formed by an insulating coating on the inside surfaces of the electrodes.

* * * * *

UNITED STATES PATENT AND TRADEMARK OFFICE
CERTIFICATE OF CORRECTION

PATENT NO. : 6,692,627 B1
DATED : February 17, 2004
INVENTOR(S) : Russell et al.

It is certified that error appears in the above-identified patent and that said Letters Patent is hereby corrected as shown below:

<u>Title page,</u>
Item [75], Inventors, "Dale R. Russell" should read -- Dale D. Russell --

Signed and Sealed this

Twenty-second Day of February, 2005

JON W. DUDAS
*Director of the United States Patent and Trademark Office*